United States Patent [19]
Dalton, Jr.

[11] 4,049,706
[45] Sept. 20, 1977

[54] SELECTIVE OXIDATION OF CHRYSANTHEMYL ALCOHOL

[75] Inventor: Augustine I. Dalton, Jr., Allentown, Pa.

[73] Assignee: Air Products and Chemicals, Inc., Allentown, Pa.

[21] Appl. No.: 616,405

[22] Filed: Sept. 24, 1975

[51] Int. Cl.$^2$ .................... C07C 51/26; C07C 45/00
[52] U.S. Cl. .............................. 260/514 H; 260/598
[58] Field of Search ........................... 260/598, 514 H

[56] References Cited

U.S. PATENT DOCUMENTS

| 3,778,477 | 12/1973 | Mueller et al. | 260/598 X |
| 3,840,566 | 10/1974 | Lalancette | 260/598 X |
| 3,926,860 | 12/1975 | Chappell | 260/514 H X |

OTHER PUBLICATIONS

Dauben et al., Jour. Org. Chem., vol. 34 (1969), 2301–2306.
Crombie et al., Jour. Chem. Soc. (1963) 4983.
Mills et al., Jour. Chem. Soc., (Perkin I) (1973) 133–137.
Heyns et al., Newer Methods of Preparative Organic Chemistry, vol. 2 (1963) 304–311, 320–323, 328–329, 332–335.

Primary Examiner—Bernard Helfin
Attorney, Agent, or Firm—Richard A. Dannells; Barry Mayerman

[57] ABSTRACT

Chrysanthemyl alcohol is selectively oxidized to the corresponding aldehyde by contact with oxygen-containing gas in the presence of supported noble metal catalyst composed of platinum on carbon. The obtained aldehyde may be further converted to chrysanthemic acid by oxidation with a solid inorganic oxidizing agent such as silver oxide in excess of stoichiometric quantity, or by reaction with a catalytic amount of oxidation promoting catalyst such as silver oxide in the presence of cupric oxide and molecular oxygen.

14 Claims, 1 Drawing Figure

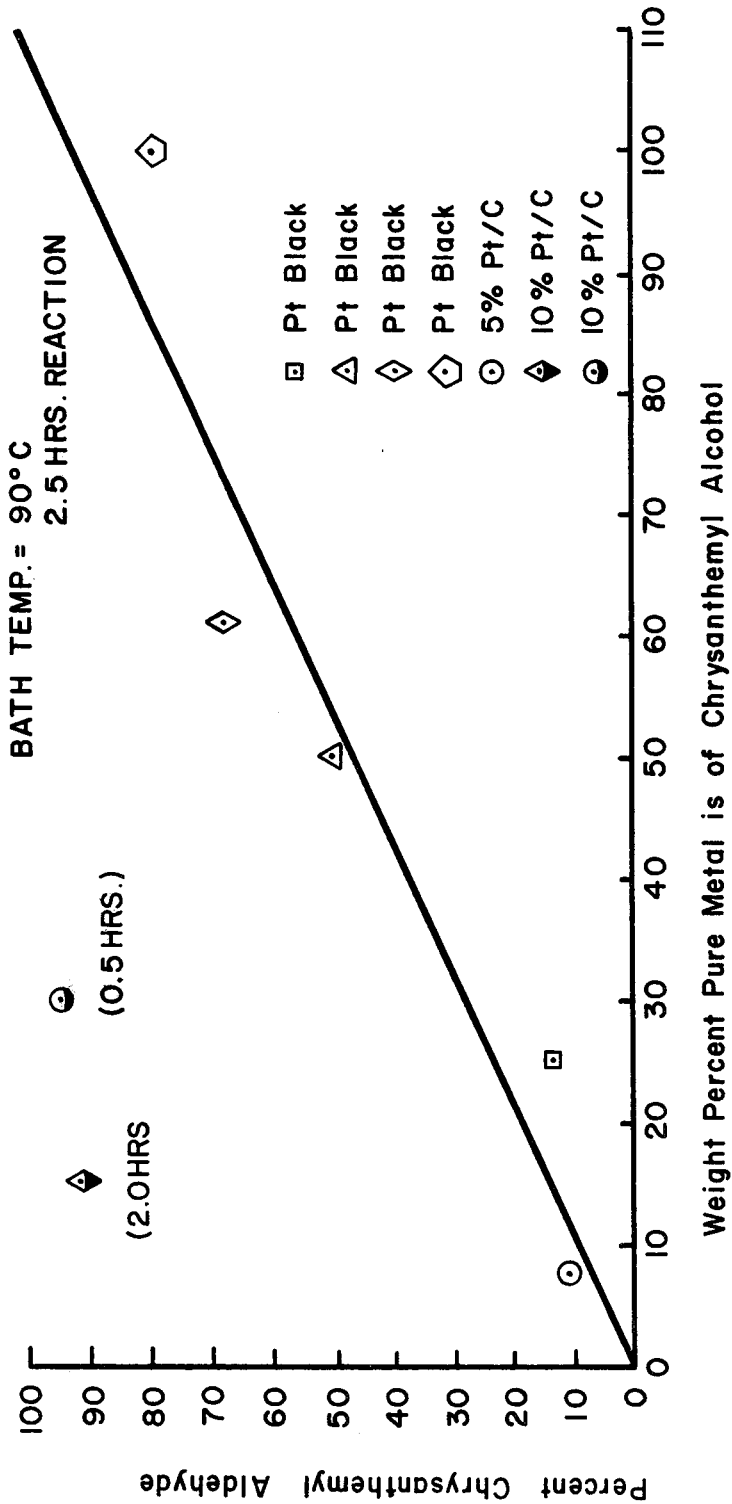

SELECTIVE OXIDATION OF CHRYSANTHEMYL ALCOHOL

BACKGROUND OF THE INVENTION

1. Field of the Invention

The present invention is concerned wih the production of chrysanthemic aldehyde by oxidation of chrysanthemyl alcohol, which aldehyde can be converted to chrysanthemic acid.

2. Description of the Prior Art

Chrysanthemic acid, pyrethric acid and their analogues are important intermediates in the production of various synthetic pyrethrins. Various methods have been reported in the literature for preparation of chrysanthemic acid and esters thereof, none of which have been found fully satisfactory for large scale commercial adoption.

More recently an asserted simplified and less expensive method for production of chrysanthemic acid and certain precursors thereof was described in published German patent application. OLS No. 2,164,024. The therein described method involves initial production of an allene intermediate by condensing, for example, dimethylallyl alcohol with an ethynyl halide to form 2-(2'-methyl propenylidene)-3,3 dimethylcyclopropylmethanol. This intermediate allene compound is converted to chrysanthemyl alcohol by reduction with sodium in liquid ammonia. To convert the obtained chrysanthemyl alcohol to the carboxylic acid, the aforesaid publication discloses the use of chromium trioxide in dry pyridine as oxidizing agent employed in considerable excess of stoichiometric requirements. The initial reaction progresses to the aldehyde stage and only after addition of a little water and stirring over a period of several days is the chrysanthemic acid formed.

It has been observed that chrysanthemyl compounds and related precursors and analogues are sensitive to acids, bases and heat. These properties preclude the use of a majority of the known catalytic and stoichiometric chemical oxidants for desired oxidation of chrysanthemyl alcohol and evidence the need for the development of oxidative procedures applicable to these alcohols, which are economically attractive for use in practical application.

A method for oxidation of chrysanthemyl alcohol to its aldehyde with potassium dichromate has been reported in the literature (Dauben, W.G. et al, *J. Org. Chem.*, 34, 2301 (1969)). The described method obtains a 31% yield of the aldehyde using an aqueous acetone solution of $H_2SO_4/K_2Cr_2O_7$. Crombie, L. et al report approximately 60% yields in the presence of a large excess of specially prepared manganese dioxide (*J. Chem. Soc.*, 4893 (1963)). The method employed in the aforesaid published German patent application, employing $CrO_3$ in aqueous pyridine, and obtaining chrysanthemic acid in moderate yields, is further described in the literature; Mills, R. W. et al., *J. Chem. Soc. (Perkin I)*, 133 (1973).

Among oxidants that have been employed or suggested for use in oxidation of simple saturated and unsaturated alcohols to corresponding aldehydes are supported and unsupported noble metal catalysts. Thus, Heyns, K. and Paulsen, H. in "Newer Methods of Preparative Organic Chemistry", 2, 303 (1963), describe catalytic oxidation of certain saturated alcohols employing unsupported platinum oxide or platinum on carbon, as well as the catalytic conversion of certain unsaturated alcohols to corresponding aldehydes over unsupported platinum oxide.

In view of the various functionalities present in chrysanthemyl alcohol sensitive to strong oxidants, such as the simultaneous presence therein of allylic hydrogen and olefinic carbon-carbon bonds, and the known rapid rearrangement of cyclopropylcarbinyl radicals and carbonium ions which are generated by certain oxidative procedures, high yields are not to be expected in the oxidation of chrysanthemyl alcohol to its aldehyde. In fact, it has been found, that chrysanthemyl alcohol decomposes even at room temperture in dilute aqueous sulfuric acid and at 125° C it is decomposed by trace amounts of chrysanthemic acid (such as would result from slight over oxidation). Vapor phase catalytic processes for oxidation of chrysanthemyl alcohol have been contraindicated because at elevated temperatures chrysanthemyl alcohol and the oxidation product aldehyde undergo thermal decomposition.

It was therefore surprising to find that exceptionally high yields of the aldehyde are selectively obtained by the oxidation of chrysanthemyl alcohol over supported platinum catalyst under the controlled conditions according to th present invention.

SUMMARY OF THE INVENTION

In accordance with the present invention the oxidation of chrysanthemyl alcohol to the aldehyde is effected in air or other free oxygen-containing gas in the presence of supported noble metal catalyst, particularly 10% or more Pt on carbon, wherein the catalyst is suspended in an essentially anhydrous organic solvent for the chrysanthemyl alcohol. Reaction is carried out at controlled temperature preferably in the range of 75° to 150° C, employing dilute solutions of the alcohol to be converted.

The application of the process of the invention to the conversion of chrysanthemyl alcohol is set out in the illustrative examples and detailed description below.

BRIEF DESCRIPTION OF THE DRAWING

The single FIGURE in the accompanying drawing is a graph demonstrating the effect of quantity of platinum on the rate of oxidation of chrysanthemyl alcohol.

DETAILED DESCRIPTION OF THE INVENTION

While conversion of chrysanthemyl alcohol to the corresponding aldehyde can be effected over unsupported platinum oxide or platinum black catalyst, or over supported platinum catalyst of lower platinum content, the full advantages of the exceptionally high yields of aldehyde at comparatively low metal/alcohol ratio are obtained when using 10% platinum on carbon. This is illustrated in the graph of the accompanying drawing.

As seen from the graph, the rate of oxidation of chrysanthemyl alcohol, as measured by the percent of aldehyde formed in the reaction mixture, increases in almost straight line proportion to the weight percent of the noble metal to alcohol. This is true whether the catalyst employed is platinum black or 5% platinum on carbon. Thus, to obtain approximately 80% aldehyde over platinum black, a 1:1 ratio of platinum to alcohol was required; at 0.5 to 1 platinum to alcohol only about 53% aldehyde was attained. These runs on the graph were carried out at a bath temperature of 90° C for a period of 2.5 hours. In the case of the catalyst comprising 10%

Pt/carbon, 90% chrysanthemyl aldehyde was obtained in two hours at 15% platinum metal by weight of alcohol; approximately 90% aldehyde was obtained in one-half hour with 10% Pt/carbon at 30% platinum to alcohol ratio.

EXAMPLE 1

In a solution of 20 grams chrysanthemyl alcohol per liter of ethyl acetate (2% w/v) there was suspended by stirring 30 grams of a catalyst composed of 10% platinum on carbon and the stirred suspension brought to reflux while passing oxygen therein through a dispersion tube at the rate of 100 cc/min. After 3 hours there was 63% conversion to aldehyde.

The reaction was continued for an additional 5 hours obtaining 82% conversion of the alcohol, at which time the reaction mixture was cooled and filtered. After removal of the solvent the organic residue was flash distilled obtaining 14.2 grams of chrysanthemyl aldehyde, constituting a selectivity of 88% at 82% conversion.

In a separate experimental run under the same conditions as above, the selectivity at 82% conversion was increased to 95% by omission of the distillation step.

EXAMPLE 2-18

Other runs were made over various catalysts under the conditions indicated in Table 1 below and with the results therein reported. The yields were determined by gas liquid partition chromatography and the reaction mixture heated at 90° C under an atmosphere of oxygen.

be taken up by the organic solvent will depend, of course, upon the solvent selected, and the solubility of water therein. In a continuous reaction process, in which the water is removed as formed, the limitation as to water solubility does not apply.

In the case of non-polar organic solvent, such as hydrocarbon solvents, very little water is taken up by the organic solvent, so that it is best to employ dilute concentrations of alcohol reactant, therein, preferably not exceeding about 4 wt.% in batch reactions. With polar solvents of the alkyl ester type such as ethyl acetate; dioxane, and the like, somewhat higher alcohol concentrations can be employed in batch reactions, but it is generally not found overall advantageous to exceed concentrations obtaining, with the catalyst ratio employed, an increasing aldehyde yield during the first hour or so, and subsequently falling off.

The unusually high yields of aldehyde, shown in the table as well as in the graph, obtained with the 10% Pt/C catalyst are not obtained with 5% Pt/C catalyst even if used in an amount to provide substantially the same metal/alcohol ratio. While the amount of Pt on the carbon support may be permitted to go one to two percent points below the preferred 10% preferably with an accompanying compensating increase in catalyst/alcohol weight ratio, no advantage is seen therein nor in increasing the percentage platinum on the carrier beyond the advocated 10%, although such increase would not be detrimental. In general, with the Pt/C catalyst of about 10% Pt on carrier, it is best employed at a catalyst to alcohol ratio providing 10 to 30% by weight of pure metal to alcohol reactant, the optimum range depending

TABLE 1

| Example | Conc. Alcohol in Solvent wt. % | Catalyst wt. % of Alcohol (Catalyst) | Solvent | % Aldehyde 1 hr. | 3 hr. | 5 hr. |
|---|---|---|---|---|---|---|
| 2* | 2 | 100 (Pt.) | heptane | 75 | 80 | 80 |
| 3* | 2 | 61 (Pt.) | heptane | 69 | 66 | — |
| 4* | 2 | 50 (Pt.) | heptane | 51 | 51 | 51 |
| 5* | 2 | 25 (Pt.) | heptane | 10 | 14 | 15 |
| 6* | 4 | 25 (Pt.) | heptane | 41 | 37 | 35 |
| 7* | 5.5 | 100 (Pt.) | heptane | 83 | 94 | — |
| 8* | 13 | 100 (Pt.) | EtOAc | 24 | 24 | 24 |
| 9* | 2 | 100 (Pt.) | EtOAc | 66 | 84 | 90 |
| 10* | 2 | 150 ( 5% Pt/C) | heptane | 6 | 12 | 16 |
| 11* | 2 | 150 ( 5% Pt/C) | EtOAc | 8 | 15 | 25 |
| 12* | 2 | 150 ( 5% Pt/C) | p-dioxane | 17 | 22 | 37 |
| 13* | 2 | 150 ( 5% Pt/C) | 2-butanone | 2 | 8 | 13 |
| 14 | 2 | 150 (10% Pt/C) | heptane | 74 | 92 | 95 |
| 15 | 2 | 150 (10% Pt/C) | EtOAc | 64 | 92 | 95 |
| 16 | 2 | 300 (10% Pt/C) | heptane | 100 | — | — |
| 17 | 2 | 300 (10% Pt/C) | EtOAc | 76 | 92 | 100 |
| 18 | 5.5 | 150 (10% Pt/C) | EtOAc | 52 | 56 | 60 |

*Controls

It will be observed from the data reported in the table for Control Examples 2-9 that high yields of aldehyde are obtained with unsupported platinum black only at metal:alcohol weight ratios of at or close to 100%; whereas for Examples 14-18 with the supported catalyst containing 10% platinum on carbon, aldehyde yields over 90% and up to 100% are obtained at a platinum metal to alcohol ratio as low as about 15%.

The table also shows the effect of increasing the concentration of alcohol in the solvent. While a limited increase in the alcohol concentration (Example 6 vs. Example 5) initially accelerated the reaction, the aldehyde yield diminished with further reaction time. This effect can be explained as probably due to the effect of free water formed as by product in the reaction beyond that amount taken up by the organic solvent. In the presence of water, acid is formed which even in small amounts inhibits the oxidation reaction in the case of water insoluble alcohols. The amount of water that can upon the solvent employed.

In a batch process for conversion of the alcohol to aldehyde over supported platinum catalyst the catalyst will lose activity with use. Such loss of activity is apparently due to the presence of that part of the product water which is insoluble in the organic solvent and because of organic acids which may be formed by over-oxidation of the aldehyde. When the activity of the catalyst falls below a desired level it can be readily reactivated by washing with polar organic solvent, such as diethyl ether, and permitted to dry.

As indicated above, the obtained chrysanthemyl aldehyde can be converted to the corresponding carboxylic acid by further selective oxidation.

After removal of solvent and solid catalyst from the liquid reaction mixture containing the chrysanthemyl aldehyde, the entire reaction product may be subjected to further oxidation if desired. However, one may first separate out at least a crude aldehyde fraction therefrom, which can be readily accomplished by chromatographic methods or other known methods of separation.

In any event, to form the desired chrysanthemic acid, the separated aldehyde fraction or the solvent-freed reaction mixture obtained by oxidation of chrysanthemyl alcohol as above described, may be oxidized with silver oxide in at least about stoichiometric quantity to the aldehyde. Another desirable alternative method is by oxidation in air or other free oxygen-containing gas in the presence of silver oxide and another oxidation catalyst of high potential. Representative illustrations of the application of these methods are given in the examples below:

EXAMPLE 19

To a stirred solution comprised of 5.3 grams NaOH in 200cc methanol there was added 60.8 grams of silver oxide ($Ag_2O$) and the mixture brought up to 73° C followed by addition of 9.8 grams chrysanthemyl aldehyde. After 1.5 hours the reaction mixture was worked up by removing the methanol on a rotary evaporator, dissolving the residue in water and recovering any neutral material (chrysanthemyl alcohol and/or aldehyde) by extraction with ether. The aqueous phase was acidified with $H_2SO_4$ and extracted with ether, dried over $MgSO_4$, and the ether removed on a rotary evaporator to give 11.8 grams of crude chrysanthemic acid. By distillation (b.p. 110°–112° C at 1.5 Torr) there was obtained 10.1 grams of pure chrysanthemic acid. This constitutes a conversion of 99% with 94% selectivity.

EXAMPLE 20

To a stirred suspension of 12.2 grams silver oxide ($Ag_2O$) and 1 gram NaOH in 40cc methanol, there was added 2 grams chrysanthemyl aldehyde in 10cc methanol at room temperature. After a short while an exothermic reaction ensued and the reaction was stopped after two hours. Workup without distillation gave 2 grams chrysanthemic acid and 0.2 grams chrysanthemyl alcohol, constituting an acid selectivity of 90% at 99+% conversion.

EXAMPLE 21

5 grams of chrysanthemyl aldehyde in 25cc methanol were added dropwise to a suspension of 0.2 grams $Ag_2O$ and 1 gram CuO in 100cc methanol containing 2.6 grams NaOH. With the mixture at 61° C, oxygen was bubbled in at the rate of 100cc/min. After about 3 hours 50% of the aldehyde had reacted to form chrysanthemic acid.

While in the foregoing example (21) the catalyst mixture employed for oxidation of the aldehyde to the corresponding carboxylic acid was silver oxide plus cupric oxide, cuprous oxide may be substituted for the latter. Moreover, the silver oxide and/or either of the oxides of copper may be deposited on an inert support such as pumice or asbestos.

While in the examples above for the formation of the aldehyde, certain polar and non-polar organic solvents are used, it will be understood that the invention is not limited to these. The preferred solvents, however, are saturated hydrocarbons boiling in the range of about 75° to 150° C and lower alkyl esters of lower saturated carboxylic acids in approximately the same boiling range. Thus, a naphtha fraction comprising of a mixture of hydrocarbons within the general boiling range specified may be conveniently employed.

Whether the catalyst for conversion of alcohol to aldehyde contains as low as 8% or the preferred 10% or more by weight of platinum metal on the carbon support, to obtain the desired selective production of high yields of the aldehyde, it is important that the ratio of platinum metal to alcohol be maintained at above 10% by weight.

What is claimed:

1. In a method of producing chrysanthemyl aldehyde comprising selectively converting chrysanthemyl alcohol to the corresponding aldehyde, the improvement which comprises contacting at a temperature in the range of 75° to 150° C the reactant alcohol dissolved in organic solvent, said alcohol being present in a range of about 2 to about 5% by weight of said solvent, with oxygen-containing gas in the presence of an amount of noble metal catalyst comprising about 10% platinum on carbon to provide a platinum metal/alcohol weight ratio of about 15% to 30% and recovering high yields of chrysanthemyl aldehyde.

2. The method as defined in claim 1 wherein said organic solvent is a polar organic solvent.

3. The method as defined in claim 2 wherein said organic solvent is a lower alkyl ester of a saturated carboxylic acid, said ester boiling in the range of 75° to 150° C.

4. The method as defined in claim 1 wherein said organic solvent is ethyl acetate.

5. The method as defined in claim 1 wherein said organic solvent is a non-polar organic solvent.

6. The method as defined in claim 5 wherein said solvent comprises one or more hydrocarbons boiling in the range of 75° to 150° C.

7. The method as defined in claim 5 wherein said organic solvent is heptane.

8. The method as defined in claim 5 wherein the concentration of reactant alcohol in said organic solvent does not exceed about 4% by weight.

9. The method as defined in claim 1 wherein the organic solvent is ethyl acetate 10. The method as defined in claim 1 wherein said organic solvent is composed of one or more hydrocarbons boiling in the range of 75° to 150° C 11. In a method of producing chrysanthemic acid which comprises selectively oxidizing chrysanthemyl alcohol to chrysanthemic acid, the improvement which comprises oxidizing at a temperature in the range of 75° to 150° C chrysanthemyl alcohol dissolved in organic solvent, said alcohol being present in a range of about 2 to about 5% by weight of said solvent, with free oxygen in the presence of an amount of supported noble metal catalyst comprising about 10% platinum on carbon to provide a platinum metal/alcohol weight ratio of about 15% to 30% to obtain a reaction product predominating in chrysanthemyl aldehyde, separating the obtained aldehyde product from the noble metal catalyst, and subjecting the same to further oxidation selectively to form chrysanthemic acid.

12. The method as defined in claim 11 wherein said further oxidation is effected by reaction with silver oxide in excess of stoichiometric amount.

13. The method as defined in claim 11 wherein said further oxidation is effected in oxygen-containing gas in the presence of oxidation promoting catalyst comprising silver oxide.

14. The method as defined in claim 11 wherein said further oxidation is effected in oxygen-containing gas in the presence of catalyst comprising silver oxide and an oxide of copper.

* * * * *